United States Patent [19]

Wierenga et al.

[11] Patent Number: 4,460,589
[45] Date of Patent: * Jul. 17, 1984

[54] PROCESS FOR TREATING HYPERTENSION

[75] Inventors: Wendell Wierenga; Harvey I. Skulnick, both of Kalamazoo, Mich.

[73] Assignee: The Upjohn Company, Kalamazoo, Mich.

[*] Notice: The portion of the term of this patent subsequent to Dec. 29, 1998 has been disclaimed.

[21] Appl. No.: 386,846

[22] Filed: Jun. 9, 1982

Related U.S. Application Data

[63] Continuation of Ser. No. 193,574, Oct. 3, 1980, abandoned.

[51] Int. Cl.³ .......................................... A61K 31/505
[52] U.S. Cl. .................................. 424/251; 544/319; 544/320
[58] Field of Search ................. 424/251; 544/319, 320

[56] References Cited

U.S. PATENT DOCUMENTS

| | | | |
|---|---|---|---|
| 2,704,285 | 3/1955 | Rorig | 260/256.4 |
| 2,723,777 | 11/1955 | Grüssner | 260/343.2 |
| 2,776,283 | 1/1957 | Rorig | 260/247.5 |
| 3,940,395 | 2/1976 | Santilli et al. | 424/251 |
| 3,956,302 | 5/1976 | Hunter et al. | 424/251 |
| 4,308,272 | 12/1981 | Wierenga et al. | 424/251 |
| 4,379,788 | 4/1983 | Heide et al. | 424/251 |

FOREIGN PATENT DOCUMENTS 882315 9/1980 Belgium .
1223686 3/1971 United Kingdom .

OTHER PUBLICATIONS

Nicols, Weed and Underwood, Antimicrobial Agents, Chem. Ther., 9 433 (1976).
Brown et al., JCS Perkin I 1023, 1975.
Sirakawa, Yakugaku Zasshi, 80 1542 1960, (CA 55 10651b).
Kulkarn et al., J. Sci. and Ind. Research (India), 19 C, 6–18 (1960).

Primary Examiner—Nicholas S. Rizzo
Attorney, Agent, or Firm—Joan Thierstein

[57] ABSTRACT

A process for treating hypertension comprising the systemic administering to a hypertensive subject or a novel compound of the formula:

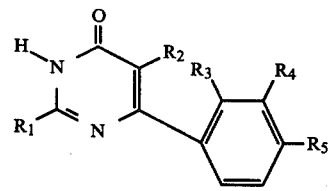

wherein
X is alkyl of from 1 to 3 carbon atoms, inclusive, or alkenyl of from 3 to 5 carbon atoms, inclusive.
$R_1$ is —$NH_2$.
$R_2$ is chloro, bromo, or iodo.
$R_3$ is hydrogen or fluorine.
$R_4$ is hydrogen or fluorine, and
$R_5$ is hydrogen, fluorine, or $CH_3$; or salt thereof, in association with a pharmaceutical carrier.

The amount administered is from 0.1 mg to 400 mg/kg of body weight, dosage unit form and dosage amounts disclosed.

4 Claims, No Drawings

PROCESS FOR TREATING HYPERTENSION

This is a continuation of application Ser. No. 193,574, filed Oct. 3, 1980, now abandoned.

DESCRIPTION

Background of the Invention

The preparation and use of 2-amino-5-halo-6-alkyl-4-pyrimidinols as antiviral agents is known (U.S. Pat. No. 3,956,302, and Nicols, Weed and Underwood, Antimicrobial Agents, Chemo. Ther. 9 433, 1976). Preparation of 2-amino-5-bromo-6-phenyl-4-pyrimidinol (V, where $X_3$ is Br and $X_1$ is phenyl) has been reported (Brown and Stevens, JCS Perkin I, 1023, 1975) but no utility has been described for this material. Snell, Elias and Freeman in Great Britain Pat. No. 1,223,686 (1967) disclose a variety of 5,6-disubstituted 2-amino-4-pyrimidinols, such as 2-dimethylamino-5-bromo-6-methyl-4-pyrimidinol. Various 5-unsubstituted 2-amino-6-arylpyrimidinols are known (e.g., Shirahawa, Yakugaku Zasshi 50, 1562, 1960, CA 55, 10651b), Kulkarui et al., J. Sci., Ind. Res. Indil. 19C, 6, 1960, and U.S. Pat. No. 2,776,283. Diuretics and cardioregulatory properties are described for various 2-amino and 2-substituted amino-5-aminomethyl and 5-aryl-6-aryl-4-pyrimidinols (U.S. Pat. Nos. 2,704,285, 2,723,777 and 2,776,283).

Related compounds wherein X is hydrogen have been described in copending U.S. application Ser. No. 022,205, filed Mar. 19, 1979, and are useful as antiviral and interferon inducing agents, or the Belgian equivalent thereof, Belgium Pat. No. 882,315.

BRIEF DESCRIPTION OF THE INVENTION

This invention relates to the treatment of hypertension with a group of novel compounds having a unique combination of pharmacological activities, namely diuretic and antihypertensive activities both of which are desirable in healing hypertensive subjects.

DETAILED DESCRIPTION

The active compounds of the present invention are represented by the formula:

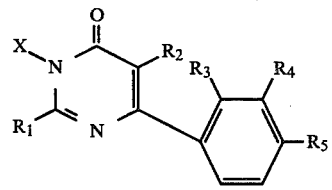

formula 1 wherein

X is alkyl of from 1 to 3 carbon atoms, inclusive, or alkenyl of from 3 to 5 carbon atoms, inclusive.

$R_1$ is $-NH_2$.

$R_2$ is chloro, bromo, or iodo.

$R_3$ is hydrogen or fluorine.

$R_4$ is hydrogen of fluorine, and $R_5$ is hydrogen, fluorine, or $CH_3$; or the salts thereof.

The compounds of the formula 1 are prepared by starting with a pyrimidinone of the formula:

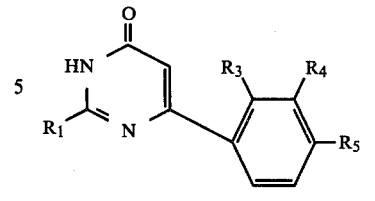

formula 2

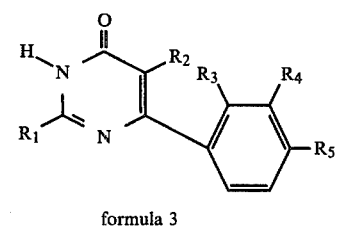

formula 3

The above compounds of the formula 2 and 3 are known and can be prepared by methods disclosed in copending U.S. Application Ser. No. 022,205, filed Mar. 19, 1979, or the Belgium equivalent thereof, Belgium Pat. No. 882,315.

Starting with a compound of the formula 2, the alkyl or alkenyl group is added at the 3-position by reacting the compound of the formula 2 with an alkyl or alkenyl halide in the presence of a base in an inert aqueous or organic solvent at ambient or reflux temperature.

Suitable solvents are water, ethanol, tetrahydrofuran and the like. Suitable bases are potassium or sodium hydroxide or the like.

The 3-alkyl, or alkenyl compound prepared is then halogenated at the 5 position, for example by treatment with N-chlorosuccinamide in acetic acid to yield the 5-chloro compound, or for example by treatment with bromine in acetic acid to yield the 5-bromo compounds, or for example by treatment with an equivalent of 1N sodium hydroxide followed by iodine in chloroform to yield the 5-iodo compound. Alternative methods of halogenation at the 5-position are disclosed in the cited U.S. application or Belgium patent.

Starting with a compound of the formula 3, the alkyl or alkenyl group is added at the 3 position by reacting the compound of the formula 3 with an alkyl or alkenyl halide in the presence of a base in an inert aqueous or organic solvent as previously described.

Salts of a compound of the formula 1 are prepared by addition of an acid having a pharmacologically acceptable anion or an alkali metal or alkaline earth base having a pharmacologically acceptable cation.

Preparation 1 2-Amino-5-iodo-3-methyl-6-phenyl-4-pyrimidinone

Part 1 3-methyl-6-phenyl-4-pyrimidinone to 7.0 g (36.4 mM) of 2-amino-6-phenyl-4-pyrimidinone was added 350 ml of abs. EtOH+3.30 g KOH (57 mM). When all the solid had dissolved, 18.2 g (7.98 ml≈0.129M) of $CH_3I$ was added and the reaction mixture heated at reflux for 5 hours. At this point an additional 0.5 g KOH was added and heating was continued for an additional 3 hours followed by the addition of 25.0 ml of $H_2O$. This mixture was cooled and evaporated to dryness under vacuum. To the solid was added 150 ml of $H_2O$, and at 50°, 1N HCl (aq) was added to dissolve solid. The solution was cooled to 20° and aq. $NaHCO_3$ solution added until no further precipitation occurred. The solids were filtered, washed well with H2O and dried at 60° C. in a vacuum oven to yield 5.4 g (74%) of title compound. Recrystallization of an analytical sample from MeOH/Et2O gave crystals, m.p. 240°–240.5° C.

Calculated for $C_{11}H_{11}N_3O$: C, 65.65-H, 5.51-N, 20.85. Found: C, 65.40-H, 5.39-N, 20.81.

NMR (D6MSO)δ: 7.88–8.05 (m, 2H, φ), 7.38–7.58 (m, 3H, φ), 7.05–7.31 (b, 2H, NH2), 6.23 (s, 1H, vinyl H), 3.33 (s, 3H, N—CH3).

Part 2  2-Amino-5-iodo-3-methyl-6-phenyl-4-pyrimidinone

To 1.8 g (8.95 mM) of 2-amino-3-methyl-6-phenyl-4-pyrimidinone was added 75 ml glacial acetic acid and 1.98 g N-iodosuccinimide (8.8 mM). The reaction mixture was heated to 70° for 5 hours. The mixture was allowed to cool to room temperature and evaporated to dryness under vacuum. The residual solid was azeotroped twice from absolute EtOH, heated to reflux with 50 ml absolute EtOH and allowed to cool to room temperature. The solids were filtered, washed well with absolute EtOH, and dried at 80° for 18 hours. Yield of yellow crystals was 1.6 g (56%).

Calculated for $C_{11}H_{10}IN_3O$: C, 40.38-H, 3.08-N, 12.83-I, 39.79. Found: C, 40.30-H, 3.31-N, 12.98-I NMR (D6MSO/TMS): 7.45 (s, 5H, φ), 3.38 (s, 3H, NCH3)

Preparation 2  5-Bromo-3-methyl-6-phenyl-4-pyrimidinone

To 1.8 g (8.95 mM) of 2-amino-3-N-methyl-6-phenyl-4-pyrimidinone was added 40 ml CH3COOH and 0.535 ml Br2 (1,64 g≈10.3 mM). The reaction mixture was allowed to stir at ambient temperature for 18 hours. The solution was evaporated to dryness and the residual solid azeotroped from EtOH (2 X). The solids were heated to reflux with 100 ml of H2O, cooled to 5° and filtered. This procedure was repeated, filtered hot, and allowed to crystallize at room temperature for 18 hours. The crystals were filtered and washed well with H2O to yield 1.0 g (40%) of title compound. Cooling of mother liquors gave an additional 0.6 g (24%) of title compound.

Calculated for $C_{11}H_{10}BrN_3O$: C, 47.15-H, 3.59-N, 15.00-Br, 28.52. Found: C, 47.14-H, 3.45-N, 15.14-Br, 28.50.

NMR(D6MSO/TMS): 7.33–7.70 (m, 5H, φ), 3.36 (s, 3H, N—CH3)

Preparation 3

Part 1

Following the procedure of the preceding Preparation 1, part 1, but substituting for the methyl iodide an equimolar amount of ethyl iodide, isopropyl iodide, or n-propyl iodide there is respectively obtained:
2-amino-3-ethyl-6-phenyl-4-pyrimidinone,
2-amino-3-isopropyl-6-phenyl-4-pyrimidinone,
2-amino-3-n-propyl-6-phenyl-4-pyrimidinone, Part 2

Following the procedure of the preceding Preparation 1, Part 2 but substituting each of the above pyrimidinones there is respectively obtained:
2-amino-5-iodo-3-ethyl-6-phenyl-4-pyrimidinone,
2-amino-5-iodo-3-isopropyl-6-phenyl-4-pyrimidinone,
2-amino-5-iodo-3-n-propyl-6-phenyl-4-pyrimidinone, Preparation 4

Part 1

Following the procedure of the preceding Preparation 1, Part 2 but substituting for the methyl iodide an equimolar amount of propenyl iodide, 2-butenyl iodide, isobutenyl iodide, or 2-pentenyl iodide there is respectively obtained:
2-amino-3-propenyl-6-phenyl-4-pyrimidinone,
2-amino-3-(2-butenyl)-6-phenyl-4-pyrimidinone,
2-amino-3-isobutenyl-6-phenyl-4-pyrimidinone,
2-amino-3-(2-pentenyl)-6-phenyl-4-pyrimidinone.

Part 2

Following the procedure of the preceding Preparation 1, Part 2 but substituting each of the above pyrimidinones there is respectively obtained:
2-amino-5-iodo-3-propenyl-6-phenyl-4-pyrimidinone,
2-amino-5-iodo-3-(2-butenyl)-6-phenyl-4-pyrimidinone,
2-amino-5-iodo-3-(isobutenyl)-6-phenyl-4-pyrimidinone,
2-amino-5-iodo-3-(2-pentenyl)-6-phenyl-4-pyrimidinone.

Illustratively, dosage levels of the administered active ingredients can be: intravenous, 0.1 to about 50 mg/kg; intraperitoneal, 0.1 to about 200 mg/kg; subcutaneous, 0.1 to about 150 mg/kg; intramuscular, 0.1 to about 150 mg/kg; orally, 0.1 to about 400 mg/kg; and preferably about 1 to 200 mg/kg; intranasal instillation, 0.1 to about 50 mg/kg; and aerosol, 0.1 to about 50 mg kg; of aniaml (body) weight.

Expressed in terms of concentration, an active ingredient can be present in the compositions of the present invention for localized use about the cutis, intranasally, pharyngolaryngeally, bronchially, bronchiolially, intravaginally, rectally, or ocularly in a concentration of from about 0.1 to about 50% w/w of the composition; preferably about 1 to about 20% w/w of the composition; and for parenteral use in a concentration of from about 0.5 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelating solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and a polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial of ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred or by dry powder for insufflation.

The active ingredients can also be admixed in animal feed. The active ingredients can conveniently be prepared in the form of a food premix. The food premix can comprise an active ingredient in admixture with an edible pharmaceutical diluent such as starch, oatmeal, flour, calcium carbonate, talc, dried fish meal and the like nontoxic, orally acceptable pharmaceutical diluents. The prepared premix is then conveniently added to the regular feed.

For use as aerosols the active ingredients can be packaged in a pressurized aerosol container together with a gaseous liquefied propellant, for example, dichlorodifluoromethane, carbon dioxide, nitrogen, propane, and the like, with the usual adjuvants such as co-solvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets teaspoonfuls, tablespoonfuls, dropperfuls, ampuls, vials, segregated multiples of any of the foregoing, and other forms as herein described.

The active ingredients to be employed as antihypertensive agents can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

EXAMPLE 1

Hard Gelatin Capsules

One thousand two piece hard gelatin capsules for oral use, each capsule containing 100 mg of 2-amino-3-methyl-5-bromo-6-metafluorophenyl-4-pyrimidinone, are prepared from the following types and amounts of ingredients:

| | |
|---|---|
| 2-Amino-3-methyl-5-bromo-6-metafluorophenyl-4-pyrimidinone, micronized | 100 gm |
| Lactose | 100 gm |
| Corn starch | 20 gm |
| Talc | 20 gm |
| Magnesium stearate | 2 gm |

The 2-amino-3-methyl-5-bromo-6-metafluorophenyl-4-pyrimidinone, finely divided by means of an air micronizer, is added to the other finely powdered ingredients, mixed thoroughly and then encapsulated in the usual manner.

The foregoing capsules are useful for preventing or treating hypertension by the oral administration of one or two capsules one to four times a day.

Using the procedure above, capsules are similarly prepared containing 2-amino-3-methyl-5-bromo-6-metafluorophenyl-4-pyrimidinone in 50 mg, and 250 mg, and 500 mg amounts by substituting 50 gm, 250 gm, and 500 gm of 2-amino-3-methyl-5-bromo-6-metafluorophenyl-4-pyrimidinone for the 100 gm used above.

EXAMPLE 2

Soft Gelatin Capsules

One piece soft gelatin capsules for oral use, each containing 250 mg of 2-amino-3-methyl-5-bromo-6-metafluorophenyl-4-pyrimidinone, finely divided by means of an air micronizer, are prepared by first suspending the compound in 0.5 ml of corn oil to render the material capsulatable and then capsulating in the above manner.

The foregoing capsules are useful as antihypertensive agents by the oral administration of one or two capsules one to four times a day.

EXAMPLE 3

Tablets

One thousand tablets, each containing 500 mg of 2-amino-3-methyl-5-bromo-6-metafluorophenyl-4-pyrimidinone, are prepared from the following types and amounts of ingredients:

| | |
|---|---|
| 2-Amino-3-methyl-5-bromo-6-metafluorophenyl-4-pyrimidinone, micronized | 500 gm |
| Lactose | 75 gm |
| Corn starch | 50 gm |
| Magnesium stearate | 4 gm |
| Light liquid petrolatum micronized | 5 gm |

The 2-amino-3-methyl-5-bromo-6-metafluorophenyl-4-pyrimidinone, finely divided by means of an air micronizer, is added to the other ingredients and then thoroughly mixed and slugged. The slugs are broken down by forcing through a number sixteen screen. The resulting granules are then compressed into tablets, each tablet containing 500 mg of 2-amino-3-methyl-5-bromo-6-metafluorophenyl-4-pyrimidinone.

The foregoing tablets are useful for treating hypertension by the oral administration of one or two tablets, one to four times a day.

Using the procedure above, tablets are similarly prepared containing 2-amino-3-methyl-5-bromo-6-metafluorophenyl-4-pyrimidinone in 250 mg and 100 mg amounts by substituted 250 gm, and 10 gm of 2-amino-3-methyl-5-bromo-6-metafluorophenyl-4-pyrimidinone for the 500 gm used above.

EXAMPLE 4

Oral Suspension

One thousand ml of an aqueous suspension for oral use, containing in each teaspoonful (5 ml) dose, 500 mg of 2-amino-3-methyl-5-bromo-6-metafluorophenyl-4-pyrimidinone, is prepared from the following types and amounts of ingredients:

| | |
|---|---|
| 2-Amino-3-methyl-5-bromo-6-metafluorophenyl-4-pyrimidinone, micronized | 100 gm |
| Citric Acid | 2 gm |
| Benzoic acid | 1 gm |
| Sucrose | 700 gm |
| Tragacanth | 5 gm |
| Lemon Oil | 2 gm |
| Deionized water, q.s. | 1000 ml |

The citric acid, benzoic acid, sucrose, tragacanth and lemon oil are dispersed in sufficient water to make 850 ml of suspension. The 2-amino-3-methyl-5-bromo-6-metafluorophenyl-4-pyrimidinone, finely divided by means of an air micronizer, is stirred into the syrup until uniformly distributed. Sufficient water is added to make 1000 ml.

The composition so prepared is useful for treating hypertension at a dose of 1 tablespoonful (15 ml) three times a day.

EXAMPLE 5

Parenteral Injectable

A sterile aqueous suspension for parenteral injection, containing in 1 ml, 300 mg of 2-amino-3-methyl-5-bromo-6-metafluorophenyl-4-pyrimidinone, is prepared from the following types and amounts of ingredients:

| | |
|---|---|
| 2-Amino-3-methyl-5-bromo-6-metafluorophenyl-4-pyrimidinone, micronized | 300 gm |
| Polysorbate 80 | 5 gm |
| Methylparaben | 2.5 gm |
| Propylparaben | 0.17 gm |
| Water for injection, q.s. | 1000 ml |

All the ingredients, except the 2-amino-3-methyl-5-bromo-6-metafluorophenyl-4-pyrimidinone, are dissolved in the water and the solution sterilized by filtration. To the sterile solution is added the sterilized 2-amino-3-methyl-5-bromo-6-metafluorophenyl-4-pyrimidinone, finely divided by means of an air micronizer, and the final suspension is filled into sterile vials and the vials sealed.

The composition so prepared is useful for treating hypertension at a dose of 1 milliliter (1 ml) three times a day.

EXAMPLE 6

Suppository, Rectal and Vaginal

One thousand suppositories, each weighing 2.5 gm and containing 150 mg of 2-amino-3-methyl-5-bromo-6-metafluorophenyl-4-pyrimidinone are prepared from the following types and amounts of ingredients:

| | |
|---|---|
| 2-Amino-3-methyl-5-bromo-6-metafluorophenyl-4-pyrimidinone, micronized | 150 gm |
| Propylene glycol | 150 gm |
| Polyethylene glycol, 4000, q.s. | 2,500 gm |

The 2-amino-3-methyl-5-bromo-6-metafluorophenyl-4-pyrimidinone is finely divided by means of an air micronizer and added to the propylene glycol and the mixture passed through a colloid mill until uniformly dispersed. The polyethylene glycol 4000 is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for treating hypertension.

EXAMPLE 7

Intranasal Suspension

One thousand ml of a sterile aqueous suspension for intranasal instillation containing in each ml 150 mg of 2-amino-3-methyl-5-bromo-6-metafluorophenyl-4-pyrimidinone is prepared from the following types and amounts of ingredients:

| | |
|---|---|
| 2-Amino-3-methyl-5-bromo-6-metafluorophenyl-4-pyrimidinone, micronized | 150 gm |
| Polysorbate 80 | 5 gm |
| Methylparaben | 2.5 gm |
| Propylparaben | 0.17 gm |

-continued

| | |
|---|---|
| Deionized water, q.s. | 1000 ml |

All the ingredients, except the 2-amino-3-methyl-5-bromo-6-metafluorophenyl-4-pyrimidinone, are dissolved in the water and the solution sterilized by filtration. To the sterile solution is added the sterilized 2-amino-3-methyl-5-bromo-6-metafluorophenyl-4-pyrimidinone, finely divided by means of an air micronizer, and the final suspension is aseptically filled into sterile containers.

The composition so prepared is useful for treating hypertension by intranasal instillation of 0.2 ml to 0.5 ml given one to four times per day.

EXAMPLE 8

Animal Feed

One thousand grams of feed premix is prepared from the following types and amounts of ingredients:

| | |
|---|---|
| 2-Amino-3-methyl-5-bromo-6-metafluorophenyl-4-pyrimidine, micronized | 20 gm |
| Soybean meal | 400 gm |
| Fish meal | 400 gm |
| Wheat germ oil | 50 gm |
| Sorghum molasses | 130 gm |

The ingredients are mixed together and pressed into pellets.

The premix can be fed to laboratory animals directly, i.e., rats and mice for treating hypertension.

For larger animals the premix can be added to the animal's regular feed in an amount calculated to give the desired dose of 2-amino-3-methyl-5-bromo-6-metafluorophenyl-4-pyrimidinone. For example, one part of premix is added to 2.5 parts of a cat's regular feed to provide the desired dose of 200 mg/kg per day for a cat of 2.5 kg.

An active ingredient can also be present, as shown in Examples 9 through 12 in the undiluted pure form for use locally about the cutis, intranasally, pharyngolaryngeally, bronchially, broncholially, or orally.

EXAMPLE 9

Oral Powder

One thousand grams of 2-amino-3-methyl-5-bromo-6-metafluorophenyl-4-pyrimidinone in bulk form is finely divided by means of an air micronizer. The micronized powder is divided into individual doses of 250 mg and packaged.

The foregoing powders are useful for treating hypertension by the oral administration of one or two powders suspended in a glass of water, one to four times per day.

EXAMPLE 10

Insufflation

One thousand grams of 2-amino-3-methyl-5-bromo-6-metafluorophenyl-4-pyrimidinone in bulk form is finely divided by means of an air micronizer.

The foregoing composition is useful for treating hypertension by the inhalation of 30 to 75 mg, one to four times per day.

EXAMPLE 11

Hard Gelatin Capsules

One thousand two-piece hard gelatin capsules for oral use, each capsule containing 100 mg of 2-amino-3-methyl-5-bromo-6-metafluorophenyl-4-pyrimidinone, are prepared from 100 grams of 2-amino-3-methyl-5-bromo-6-metafluorophenyl-4-pyrimidinone.

The 2-amino-3-methyl-5-bromo-6-metafluorophenyl-4-pyrimidinone is finely divided by means of an air micronizer and encapsulated in the usual manner.

The foregoing capsules are useful for treating hypertension by the oral administration of one or two capsules, one to four times a day.

Using the procedure above, capsules are similarly prepared containing 2-amino-3-methyl-5-bromo-6-metafluorophenyl-4-pyrimidinone in 50 mg, 250 mg, and 500 mg amounts by substituting 50 gm, 250 gm, and 500 gm of 2-amino-3-methyl-5-bromo-6-metafluorophenyl-4-pyrimidinone for the 100 gm used above.

EXAMPLE 12

Following the procedure of the preceding Examples 1 through 11, inclusive, compositions are prepared substituting equivalent amounts of the pharmaceutically acceptable acid addition salts of 2-amino-3-methyl-5-bromo-6-metafluorophenyl-4-pyrimidinone for the free base of the examples.

EXAMPLE 13

Following the procedure of the proceding Examples 1 through 11, inclusive, compositions are prepared substituting equivalent amounts of 2-amino-3-methyl-5-bromo-6-metafluorophenyl-4-pyrimidinone or the pharmaceutically acceptable acid addition salts or the alkali metal or alkaline earth metal salts of each of the foregoing compounds for 2-amino-3-methyl-5-bromo-6-metafluorophenyl-4-pyrimidinone of each of the examples. Those compositions are useful for treating hypertension where administered as described above and in Examples 1 through 12, inclusive.

We claim:

1. A process for treating hypertension comprising the administration to a hypertensive subject a compound of the formula

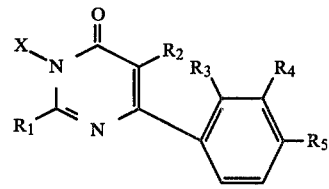

wherein X is alkyl of from 1 to 3 carbon atoms, inclusive, or alkenyl of from 3 to 5 carbon atoms, inclusive,
$R_1$ is $-NH_2$,
$R_2$ is chloro, bromo or iodo,
$R_3$ is hydrogen or fluorine,
$R_4$ is hydrogen or fluorine, and
$R_5$ is hydrogen, fluorine or $CH_3$; or a salt thereof; in association with a pharmaceutical carrier.

2. The process of claim 1 wherein the amount administered is from 0.1 mg to 400 mg/kg of body weight.

3. The process of claim 2 wherein the compound administered is 2-amino-3-methyl-5-bromo-6-phenyl-4-pyrimidinone.

4. The process of claim 2 wherein the compound administered is 2-amino-3-methyl-5-bromo-6-metafluorophenyl-4-pyrimidinone.

* * * * *